United States Patent [19]
Williams, Jr.

[11] Patent Number: 5,716,396
[45] Date of Patent: Feb. 10, 1998

[54] ENDOPROSTHESIS HAVING MULTIPLE LASER WELDED JUNCTIONS METHOD AND PROCEDURE

[75] Inventor: Norman F. Williams, Jr., Miami, Fla.

[73] Assignee: Cordis Corporation, Miami Lakes, Fla.

[21] Appl. No.: 491,279

[22] Filed: Jun. 16, 1995

Related U.S. Application Data

[63] Continuation of Ser. No. 123,440, Sep. 16, 1993, abandoned.

[51] Int. Cl.$^6$ .................................................. A61F 2/06
[52] U.S. Cl. ................................................. 623/1; 623/12
[58] Field of Search .................................. 623/1, 11, 12; 604/281, 282; 606/194, 195

[56] References Cited

U.S. PATENT DOCUMENTS

| | | |
|---|---|---|
| 4,000,392 | 12/1976 | Banas et al. . |
| 4,078,167 | 3/1978 | Banas et al. . |
| 4,127,761 | 11/1978 | Pauley et al. . |
| 4,503,569 | 3/1985 | Dotter . |
| 4,553,545 | 11/1985 | Maass et al. . |
| 4,580,568 | 4/1986 | Gianturco . |
| 4,649,922 | 3/1987 | Wiktor . |
| 4,655,771 | 4/1987 | Wallsten . |
| 4,655,776 | 4/1987 | Lesinski . |
| 4,658,110 | 4/1987 | Miller et al. . |
| 4,733,665 | 3/1988 | Palmaz . |
| 4,738,389 | 4/1988 | Moshier et al. . |
| 4,739,762 | 4/1988 | Palmaz . |
| 4,776,337 | 10/1988 | Palmaz ...................... 623/1 X |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,913,141 | 4/1990 | Hillstead . |
| 4,922,905 | 5/1990 | Strecker . |
| 4,969,458 | 11/1990 | Wiktor . |
| 4,994,071 | 2/1991 | MacGregor . |
| 5,015,253 | 5/1991 | MacGregor ...................... 623/1 |
| 5,019,085 | 5/1991 | Hillstead . |
| 5,019,090 | 5/1991 | Pinchuk . |
| 5,035,706 | 7/1991 | Gianturco et al. . |
| 5,037,427 | 8/1991 | Harada et al. . |
| 5,041,126 | 8/1991 | Gianturco . |
| 5,092,877 | 3/1992 | Pinchuk ...................... 623/1 |
| 5,133,732 | 7/1992 | Wiktor . |
| 5,135,536 | 8/1992 | Hillstead ...................... 606/195 |
| 5,161,547 | 11/1992 | Tower ...................... 128/898 |

(List continued on next page.)

FOREIGN PATENT DOCUMENTS

| | | | |
|---|---|---|---|
| 540290 | 5/1993 | European Pat. Off. ...................... 623/1 |
| 556850 | 8/1993 | European Pat. Off. ...................... 623/1 |
| 565251 | 10/1993 | European Pat. Off. . |

OTHER PUBLICATIONS

Van Nostrand's Scientific Encyclopedia, 6th Edition, "Welding", pp. 3007–3008.

*Primary Examiner*—Michael J. Milano
*Attorney, Agent, or Firm*—Lockwood, Alex, Fitzgibbon & Cummings

[57] ABSTRACT

An endoprosthesis is provided which presents an endoprosthesis body of a helically wound strand of generally malleable material exhibiting a repeating pattern of undulations that follow a generally helically wrapped axis. Adjacent full circle windings each have at least one weld joining together apex-like portions of adjacent full circle windings. In a preferred arrangement, a plurality of these welds define a substantially in-line helical pattern of welds along the endoprosthesis or stent. One, two, three or more of these substantially in-line helical patterns of welds can be provided. Also provided is a method for forming the endoprosthesis which includes fusion welding, typically within an inert gas atmosphere and in a manner such that the entirety of the stent lies along the same generally cylindrical three-dimensional plane. A procedure is included whereby the endoprosthesis or stent is implanted by deployment with a suitable expansion device, the deployment expanding the pattern of undulations in a uniform manner to provide an especially consistent support surface throughout the endoprosthesis.

15 Claims, 3 Drawing Sheets

U.S. PATENT DOCUMENTS

| | | | |
|---|---|---|---|
| 5,304,200 | 4/1994 | Spaulding | 606/198 |
| 5,314,472 | 5/1994 | Fontaine | 623/12 |
| 5,354,309 | 10/1994 | Schnepp-Pesch et al. | 606/198 |
| 5,370,683 | 12/1994 | Fontaine | 623/1 |
| 5,421,955 | 6/1995 | Lau et al. | 216/48 |
| 5,443,498 | 8/1995 | Fontaine | 623/1 |

ENDOPROSTHESIS HAVING MULTIPLE LASER WELDED JUNCTIONS METHOD AND PROCEDURE

This application is a continuation of application Ser. No. 123,440, filed Sep. 16, 1993 now abandoned.

BACKGROUND AND DESCRIPTION OF THE INVENTION

The present invention generally relates to endoprostheses, also known as stents, and to their preparation and use. More particularly, the invention relates to endoprostheses having multiple welded junctions which join adjacent windings composed of undulating bendable segments which are oriented in a generally helical pattern along the length of the endoprosthesis. The bendable segments impart radial expandability to the endoprosthesis, which can be tailored so as to vary the hoop strength of the endoprosthesis while still retaining the ability of the endoprosthesis to follow the contour of the vessel within which it is to be deployed. Endoprostheses according to the invention also exhibit exceptional uniformity of expansion and maintain the desired solid surface area percentage substantially throughout the entirety of the endoprosthesis, particularly after deployment.

Various endoprosthesis devices or stents have been developed or proposed for use in association with angioplasty treatments and other medical treatments or procedures wherein devices having expandable components, such as balloon catheters, are used to treat a condition with a body vessel. The endoprosthesis or stent is in the nature of a device, usually tubular or cylindrical in shape, which is deployed by a balloon or otherwise and which remains within the vessel at a treatment location upon withdrawal of the balloon catheter or other deployment and/or treatment device.

Exemplary patents in this regard include Pinchuk U.S. Pat. Nos. 5,019,090 and 5,092,877, MacGregor U.S. Pat. Nos. 4,994,071 and 5,015,253, Hillstead U.S. Pat. Nos. 4,856,516 and 4,913,141, and Gianturco U.S. Pat. Nos. 4,580,568 and 4,800,882. Certain endoprostheses or stents, such as those illustrated in Dotter U.S. Pat. No. 4,503,569, Wallsten U.S. Pat. No. 4,655,771 and Palmaz U.S. Pat. No. 4,733,665 present devices that have no or very limited compliance characteristics. They are not, for example, particularly well-suited for "stenting" body passageways having configurations which are not substantially linear. For example, stenting curved vessel pathways with endoprostheses that present a generally rigid cylindrical shape typically requires endoprostheses that are very short in length and that are strung out along the curved pathway, with each such endoprosthesis engaging an adjacent endoprosthesis along respective edges of the endoprostheses, thereby leaving a gap between each pair of endoprostheses at the outside radius of the curved vessel being stented. Also, such endoprostheses often will be delivered separately, thereby increasing the invasiveness of the procedure. In other endoprostheses, concerns can be raised that the body of the endoprosthesis stretches along its longitudinal axis during use. For example, Wiktor U.S. Pat. No. 5,133,732 proposes longitudinal over-stretch limiting means such as by attaching a longitudinal wire generally parallel to the axis of the endoprosthesis.

Accordingly, previous approaches in the endoprosthesis or stent art have proposed or provided devices having good hoop strength, which can be particularly important in stenting applications which could be subjected to forces tending to collapse the endoprosthesis, such as when relatively large vessels are stented or when the stent is deployed within a vessel susceptible to external forces, such as within the leg. Other known endoprostheses or stents exhibit less hoop strength but are more compliant in that they are better suited to conform to the contour of the vessel, rather than being so non-conforming as to mis-shape the vessel after deployment. A typical disadvantage of the more-compliant stent devices is that they tend to deform upon or after deployment and present stenting surfaces that can lack desirable uniformity throughout the working surface area of the stent. Development of non-uniformity in the working surface area of the stent can be especially evident during expansion of the stent from its collapsed, insertion diameter to its expanded, implanted diameter. At times, this lack of uniformity upon expansion is exacerbated by folds or other non-uniformities in a balloon on which the stent is mounted for deployment.

It has been found that the endoprostheses in accordance with the present invention exhibit the ability to follow the contour of the vessel being stented while still exhibiting the hoop strength needed for adequate support such as that provided by less compliant structures including those of the Palmaz type as discussed herein, while providing the additional advantage of ensuring uniform expansion to provide an expanded stent that exhibits the desired percentage of support surface area. Furthermore, with the present invention, these important properties can be tailored to fit the particular needs of the problem being addressed by varying compliance and hoop strength as needed.

In summary, the present invention achieves these advantages and advances the endoprosthesis art by an endoprosthesis constructed of a strand having bendable segments organized in an undulating and substantially uniform fashion, which undulating strand is wound in a generally helical configuration to form the endoprosthesis body composed of a plurality of full circle windings continuous with each other along the helical path. In general, the undulations of adjoining windings generally line up with one another to either contact one another or be closely spaced from one another. At selected ones of these locations, welds are applied in order to thereby join adjacent windings. At least one weld is positioned along each winding. In an especially preferred embodiment, the welds are oriented with respect to each other so as to form a helical pattern of welds along the endoprosthesis.

It is accordingly a general object of the present invention to provide an improved endoprosthesis having multiple welded junctions and the making and use of same.

Another object of the present invention is to provide an improved endoprosthesis or stent that exhibits good strength while having the ability to follow the contour of the vessel within which it is implanted.

Another object of this invention is to provide an improved endoprosthesis that minimizes the risk of developing intimal hyperplasia or irritation brought on by its deployment within a living vessel and the method associated therewith.

Another object of the present invention is to provide an improved endoprosthesis and deployment procedure whereby the stent overlaps by at least about 0.5 cm both sides of the dissection being treated, even in the case of an elongated dissection that does not exhibit a straight contour.

Another object of this invention is to provide an improved endoprosthesis and method to provide a stent that has an integrity comparable to that of a much less flexible stent while still exhibiting flexibility required in many uses, including within coronary vessels.

Another object of the present invention is to provide an endoprosthesis having multiple fusion welded junctions which exhibit a flexibility reduced by only about 10 to 15% of a similar device without welded junctions and while simultaneously providing the integrity of stent structures exhibiting much less flexibility or compliance properties.

Another object of this invention is to provide an improved stent or endoprosthesis and use thereof with exceptional uniformity in presentation of supporting surface area throughout the working surface of the stent.

Another object of the present invention is to provide an improved endoprosthesis or stent which reduces in length when expanded during deployment, while increasing the pitch of the helix that broadly defines the configuration of the endoprosthesis.

Another object of the present invention is to provide an improved endoprosthesis or stent which, when deployed, avoids overlap of stent structural components to thereby provide a stent having minimal thickness throughout the stent to reduce the likelihood of accelerated hyperproliferation or thicker cell growth as a protection response to a thickened wall surface.

Another object of the present invention is to provide endoprostheses and manufacture thereof while tailoring same for desired end uses, including vascular, bronchial, tracheal, urological, rectal, transinterhepactic shunting, bilary tree, and the like.

Another object of this invention is to provide an improved endoprosthesis having multiple welded junctions which substantially reduce external expansion of a stent when deployed within vessels having curved contours.

These and other objects, features and advantages of this invention will be clearly understood through a consideration of the following detailed description.

BRIEF DESCRIPTION OF THE DRAWINGS

This invention is further elucidated in the following description with reference to the annexed drawings, wherein.

DESCRIPTION OF THE PARTICULAR EMBODIMENTS

Figure 1:
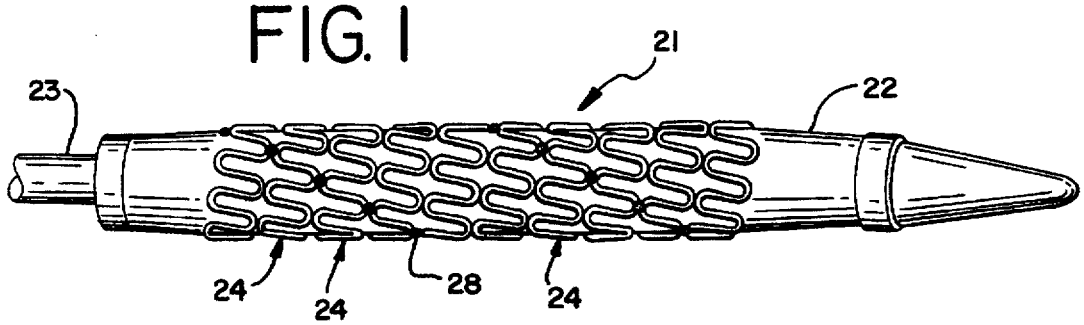
FIG. 1 is a perspective view of a portion of a balloon catheter having an endoprosthesis in accordance with the present invention positioned thereon for subsequent deployment.

FIG. 1 depicts an endoprosthesis or stent in accordance with the present invention, generally designated as 21, positioned over a balloon component 22 of a catheter 23 of generally known construction. The balloon is illustrated in a deflated condition, with the endoprosthesis closely lying thereover. As is well known in the art, when a suitable fluid such as saline solution is passed into the catheter under pressure, the balloon component 22 expands, thereby radially expanding the endoprosthesis 21. Typically, this expansion is carried out within a body vessel, such as within a blood vessel, coronary passageway, bilary duct or other body vessel.

The expansion is initiated after the balloon and endoprosthesis are positioned within the vessel so as to be radially spaced away from a diseased or damaged area of the vessel. Upon radial expansion as described, the balloon deploys the endoprosthesis to engage and support the diseased or damaged portion. It has been found that the effectiveness of this stenting procedure is particularly enhanced when the endoprosthesis traverses a length greater than the length of the diseased section so that there is an overlap of at least about 0.5 cm of endoprosthesis beyond each end of the diseased or damaged sections. Accordingly, the deployment procedure according to the invention includes providing an endoprosthesis having a length greater than the length of the diseased area when the endoprosthesis is positioned along the diseased area, taking into consideration changes in contour of the vessel at the diseased section.

With more particular reference to the endoprosthesis 21, the illustrated embodiments include a strand of metal or polymer which exhibits malleability adequate to be formed into shapes such as those illustrated, retain those shapes, and expand as discussed herein when subjected to radial outwardly directed forces. In the illustrated embodiment, the strand is formed into bendable segments to provide a repeating pattern of undulations. The undulating strand is shaped into a plurality of full circle windings 24 that are wrapped through 360°. Each winding includes a plurality of bendable segments 25. Each bendable segment includes legs 26 joined by a connecting portion 27. In the embodiment shown in the drawings, legs 26 and connecting portions 27 define a sinusoidal curve which can be shaped as illustrated in the drawings or take on somewhat different shapes. In this regard, and with regard to the manner in which the undulating winding can be formed, reference is made to Pinchuk U.S. Pat. No. 5,019,090, the subject matter thereof being incorporated by reference hereinto.

Figure 2:
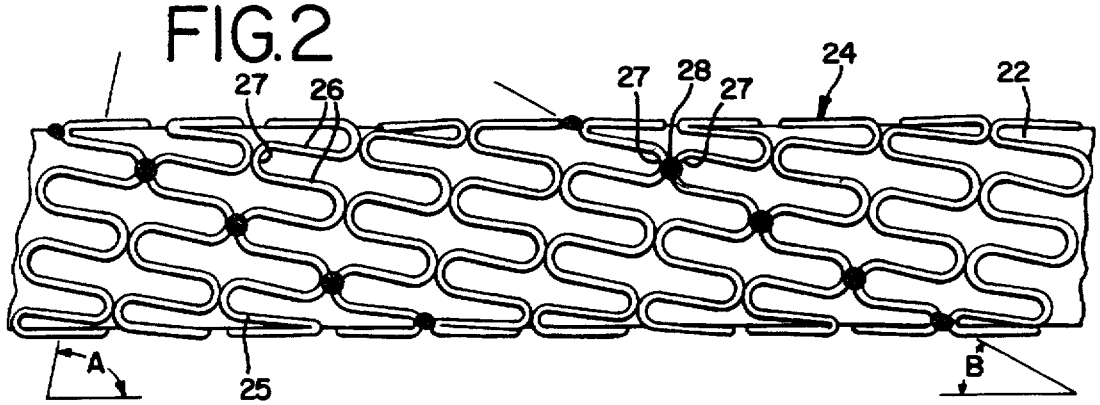
FIG. 2 is a enlarged elevational view illustrating the embodiment shown in FIG. 1 which includes two helically oriented spines defined by a plurality of welds positioned along the endoprosthesis.
Figure 4:
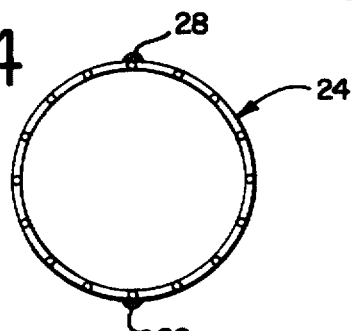
FIG. 4 is an end view of the embodiment shown in FIG. 2.

A plurality of welds 28 join adjacent pairs of connecting portions 27. In accordance with the invention, at least one weld 28 joins each winding 24 to the winding or windings adjacent thereto. While the helix winding angle "A" of the windings as shown in FIG. 2 is relatively steep with respect to the longitudinal axis of the endoprosthesis 21, the pitch angle "B" of the plurality of welds 28 is relatively shallow. It will be noted that pitch angle "B" follows the pitch angle defined by adjacent connecting portions 27 of adjacent windings 24. Accordingly, the pitch angle "B" of the illustrated helical weld pattern follows the pitch angle of the wrapped helix that is defined by adjacent connecting portion pairs. As perhaps best illustrated in FIG. 4, this embodiment includes two such generally helical weld patterns which generally parallel each other and which are longitudinally spaced from one another.

Figure 3:
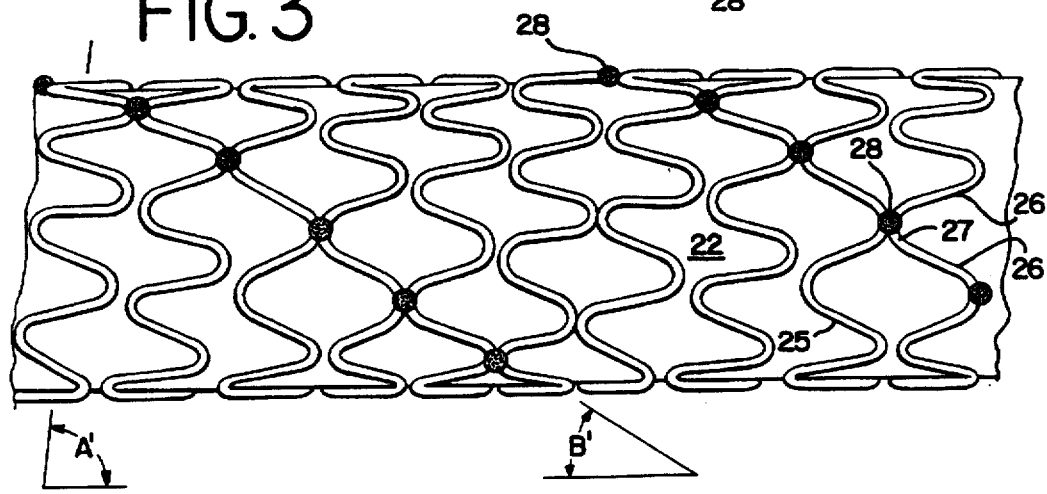
FIG. 3 is an elevational view of the embodiment shown in FIG. 2 wherein the endoprosthesis has been expanded for deployment.

It will be noted from FIG. 3 that, after expansion, the overall length of the endoprosthesis 21 is decreased, while the helix winding angle "A'" is steeper than that of the helix winding angle "A" prior to expansion, and the pitch angle "B'" after expansion is steeper than the pitch angle "B" prior to expansion. For example, a particular size of such an endoprosthesis can have an unexpanded diameter of 8 mm and an unexpanded length of 3 cm. After a typical expansion to 12 mm, its length is about 2.7 cm, with the helix winding angle and pitch angle being changed accordingly.

It will further be noted that each of the bendable segments 25 has opened up to substantially the same extent, with each leg 26 being spaced farther from each of its adjoining legs than prior to expansion, this opened spacing being substantially uniform throughout each winding of the endoprosthesis. Each weld 28 remains along the helical pathway even after the endoprosthesis is expanded. This can be generally referred to as sinusoidal expansion which the invention achieves even with pleated balloons that can tend to cause non-sinusoidal expansion of other stents such as non-welded stents or more rigidly joined stents, wherein one leg of the bendable segment expands readily while its other leg movement is dampened.

Figure 8:
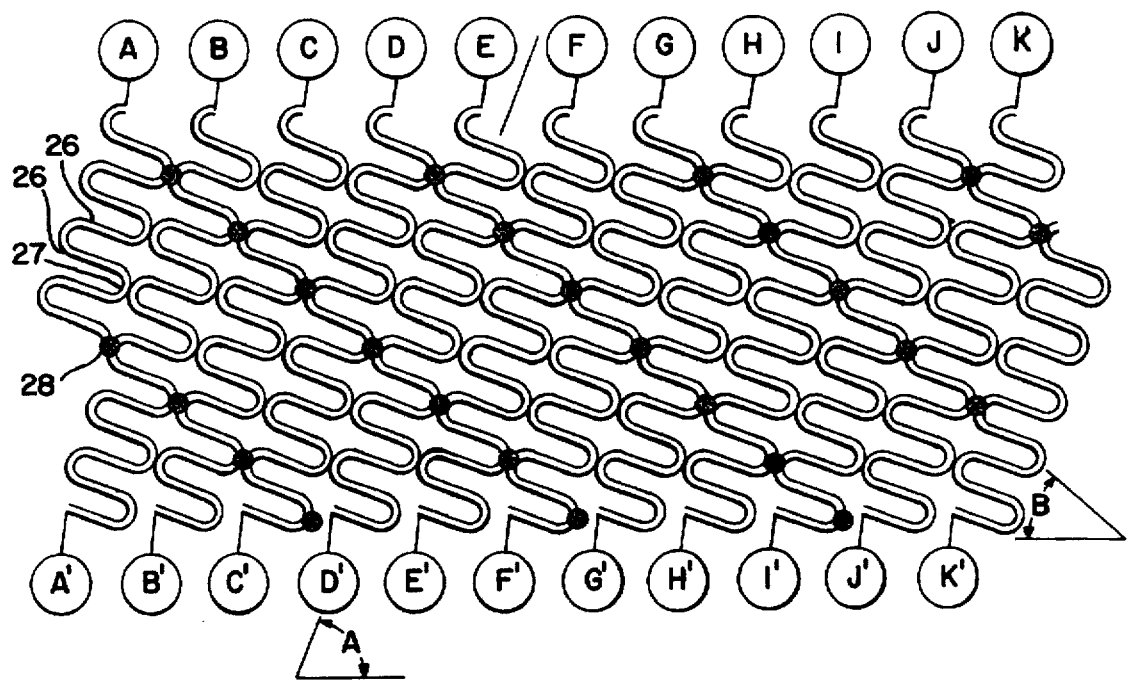
FIG. 8 is a schematic illustration of the embodiment shown in FIGS. 1 through 4 wherein the endoprosthesis has been severed longitudinally and flattened for illustrative purposes.
Figure 9:
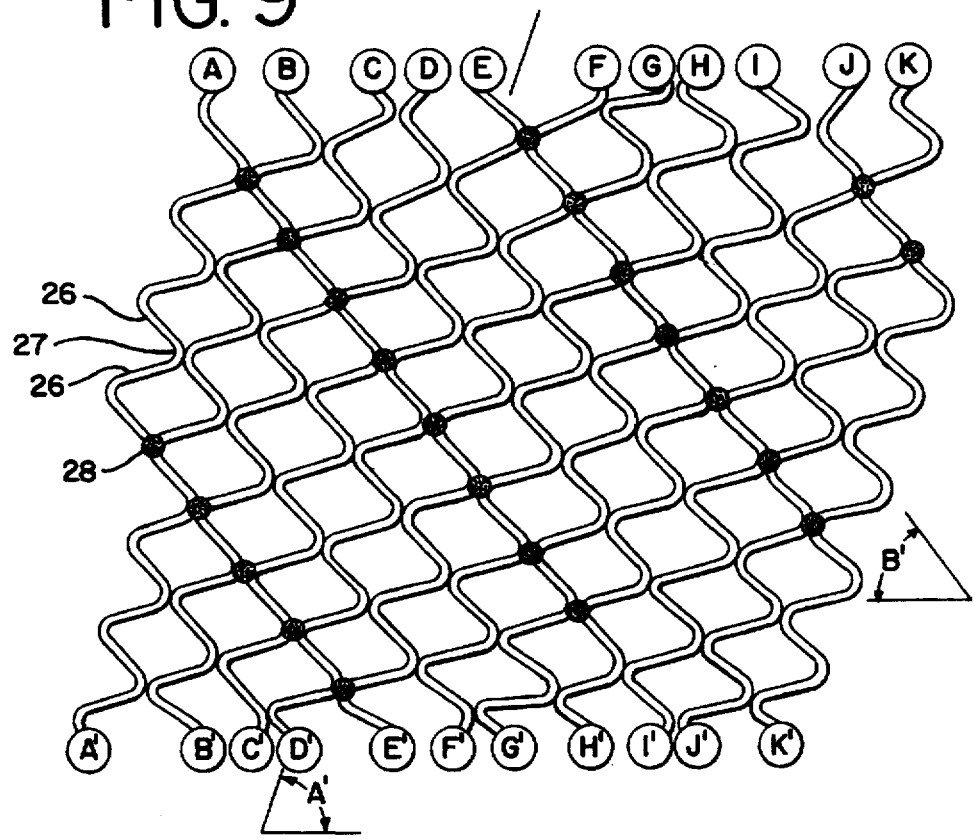
FIG. 9 is a schematic view as shown in FIG. 8 in its expanded orientation.

Because of this uniform type of expansion, the unexpanded as well as the expanded supporting surface area of the endoprosthesis is substantially consistent throughout the endoprosthesis. This is perhaps even better illustrated in the flattened depiction of this embodiment that is shown in FIG. 8 and FIG. 9 without the optical distortion present in the other figures due to the curvature of the cylindrical endoprosthesis. For example, FIG. 9 shows the uniform nature of the expanded supporting surface area.

Figure 5:
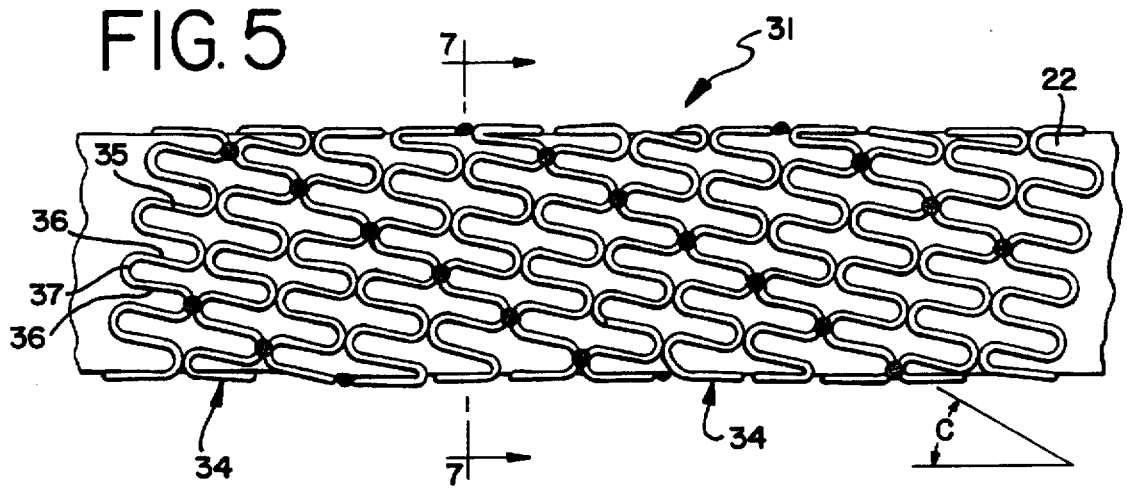
FIG. 5 is an elevational view of another embodiment of the present invention having three separate helically oriented spines defined by a plurality of welds aligned along three generally helical paths.
Figure 7:
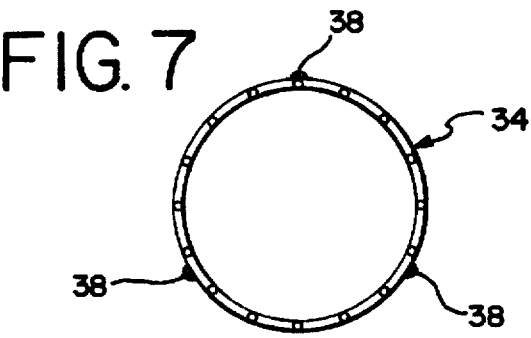
FIG. 7 is an end view of the embodiment illustrated in FIG. 5.
Figure 6:
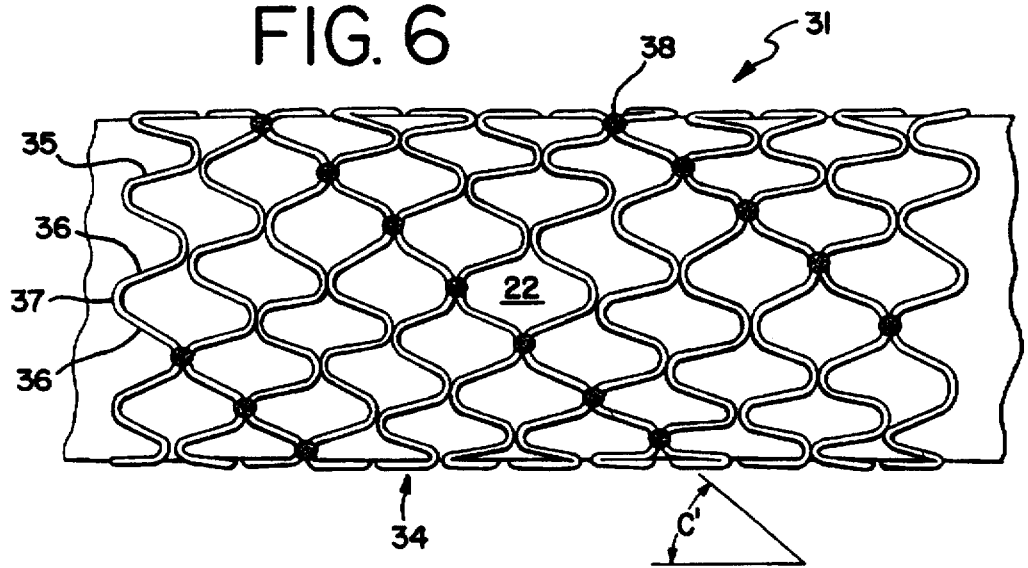
FIG. 6 is an elevational view of the embodiment illustrated in FIG. 5 shown in its expanded position for deployment.

With reference to the embodiment illustrated in FIGS. 5, 6 and 7, endoprosthesis or stent 31 is composed of a plurality of windings 34 having a plurality of bendable segments 35 having legs 36 and a connecting portion 37. In this embodiment, welds 38 are aligned along three helical pathways which follow pitch angle "C" when unexpanded as illustrated in FIG. 5 and pitch angle "C'" as illustrated in FIG. 6.

In these illustrated embodiments, thirteen welds are provided for each inch of length of endoprosthesis per helical pathway or "spine." Accordingly, in the two helix or "double spine" embodiment illustrated in FIGS. 1 through 4, twenty-six welds are provided for each longitudinal inch of endoprosthesis. In the three helix or "triple spine" embodiment illustrated in FIGS. 5, 6 and 7, there are thirty-nine welds per longitudinal inch of endoprosthesis and the winding mandrel can be larger than for the double spine embodiment.

While the illustrated preferred embodiments show the plurality of welds oriented in a helical manner along a generally continuous pathway or helical spine, other weld orientations are also possible. For example, one of the weld spines of a multiple-spine configuration can omit welds therealong, such that every other adjacent pair of connecting portions along this interrupted helical spine can remain unwelded. Again, in a multiple-spine configuration, alternating connecting portion adjacent pairs can remain unwelded, preferably staggered in such a manner that each adjacent winding is secured together at its other adjacent winding or windings by at least one weld at a connecting portion pair. It is possible to form helical spines in an orientation other than that as illustrated which follows the pitch angle of the wrapped helix, for example weld spine patterns that are generally parallel to the axis of the endoprosthesis and weld spine patterns that follow a counter-clockwise oriented helix, rather than the clockwise oriented helical spine illustrated in the drawings. In addition, although the drawings illustrate endoprostheses having two or three in-line weld spine patterns, patterns having a single spine and having four or more spines are also possible.

The embodiments illustrated in the drawings are preferred, primarily because of the uniform expansion experienced when these endoprostheses are deployed by a balloon catheter. By following the pitch angle of the wrapped helix of the endoprosthesis, and by providing weld spine patterns that provide a weld at each connecting portion pair therealong, a particularly even pull is experienced on each leg 26, 36 when the endoprosthesis is expanded for deployment. Particularly uniform stretching is experienced, which is important to the operative functional advantages of the endoprostheses according to the invention.

More specifically, it is at present generally accepted that the supporting surface area (typically the "metal" outside or working surface of the stent) is to constitute between about 12% and about 15% of the cylindrical surface defined by the stent. Otherwise, inadequate support will be provided. This means that, under present beliefs, it is desirable to have between about 85% and about 88% open space presented by the external cylindrical definition of the stent. The configuration of the stent of the invention is tailored to fall within these guidelines. More importantly, the present invention provides a structure wherein the amount of supportive surface area or "metal" presented to the vessel by the stent is a consistent percentage throughout the length and circumference of the stent. Accordingly, if 12 to 15% supporting surface area is provided by the stent, all portions of the cylindrical stent surface, both before expansion and when expanded as deployed, presents a supporting surface area within this percentage range. This uniformity of supporting surface is important. This feature, for example, avoids the undesirable situation where a stent might meet the 12 to 15% guideline when the entirety of the stent surface is averaged, but might be considerably below the guideline percentage at the very location along the stent where support is most needed. Similarly, if certain locations of the stent present too great a percent of support surface or metal, accelerated hyperproliferation could occur, resulting in cell growth that is thicker than desired at these locations of excess support surface, resulting in a narrowing of the body passageway at this location.

Endoprostheses made in accordance with the present invention are also particularly well-suited for deployment within vessels having curved contours. It will be appreciated that the combination of unwelded connecting portion pairs and welded connecting portion pairs permit the endoprosthesis to lie within and follow a curve in a vessel without presenting excessive spacing between unwelded connecting portion pairs, for example at an outside or larger radius curve. It has been found that, in similar stent structures without the weld pattern, the outside curve of the endoprosthesis will open about two times to three times the spacing between adjacent windings when unexpanded and longitudinal. The present invention dampens that expansion by at least approximately 60% to 70% while still permitting the endoprosthesis to follow the natural contour of the vessel. This results in a marked reduction in excess free space presented by the outside curve of the endoprosthesis. In addition, the weld pattern helps to prevent excessive overlap of endoprosthesis strand material at the inside curve of the vessel contour.

With more particular reference to the welds 28, 38, they are preferably formed by a fusion welding procedure, such as electron beam welding, laser welding, TIG welding and the like. Welding in inert gas environments or under vacuum conditions is particularly desirable for materials such as tantalum which have a great affinity for oxygen, hydrogen and the like in that metals actively absorb gases such as oxygen. Accordingly, when welding is carried out in the presence of even small amounts of oxygen or other gases having a strong affinity for tantalum or the like, an embrittlement at the weld is experienced. It is believed that the onset of such embrittlement conditions is especially likely during an operation such as fusion welding wherein a metal is rapidly heated and quickly cooled thereafter. The welds according to the present invention are preferably carried out within an enclosure which provides a consistent environment of inert gas such as argon, helium or other members of the inert gas family including those specified in the inert gas grouping of the periodic table. It is especially preferred that the inert gas be contained within the enclosed compartment during welding and that the compartment be filled with inert gas, as opposed to a situation where inert gas is directed by means of a gas flow past an open welding area. It has been found to be important to maintain the inert gas environment within the compartment while preventing influx of air or other oxygen source. The fusion welding energy source typically is directed onto the location of the connecting portion pairs.

Strand material out of which the endoprostheses according to the invention are made must be capable of forming a joint under welding or heating conditions. In addition, the strand material should have malleability characteristics. Included are tantalum, titanium, silver, gold, annealed elastic metal materials, and alloys containing same. Polymers may also be used, such as polyether sulfone, polyimides, polycarbonates, polypropylenes, high molecular weight polyethylenes, carbon fibers, Kevlar polymer, and the like. It is also possible to coat these materials after stent formation has been completed with porous or textured surfaces for cellular ingrowth and the like or with non-thrombogenic agents such as pyrolytic carbon, heparin, hydrogels, Teflon materials, silicones, polyurethanes and the like. Treatments can also be carried out so that drugs or medicines can be eluted therefrom. It is also possible that certain stents may be made of biodegradable materials. The strand material must, of course, be biocompatible. Tantalum is the especially preferred strand material. For example, materials such as tantalum have the ability to be plasticly deformed without significantly compromising the strength of the metal. Such a property is typically not provided by more elastic materials such as stainless steel which, once bent, will lose a noticeable percentage of its strength.

It will be understood that the embodiments of the present invention which have been described are illustrative of some of the applications of the principles of the present invention. Numerous modifications may be made by those skilled in the art without departing from the true spirit and scope of the invention.

I claim:

1. An implantable transluminal endoprosthesis, comprising:

a strand wound in a generally helical configuration to form an endoprosthesis having a plurality of full circle windings that are wrapped through 360° and which are substantially continuous with each other along a generally helically wrapped axis;

said wound strand including a repeating pattern of undulations that follow said generally helically wrapped axis, said pattern of undulations having a plurality of substantially equally sized and shaped bendable segments, said bendable segments having legs alternating with bendable connecting portions to impart radial expandability to the endoprosthesis, the endoprosthesis having an unexpanded transluminal insertion circumference and an expanded deployed circumference which is greater than said unexpanded circumference;

said plurality of full circle windings are generally adjacent to each other and respective ones of said bendable connecting portions of adjacent full circle windings are adjacent to each other so as to define adjacent bendable connecting portions;

said bendable segments are positioned in a generally closed orientation with respect to each other at said unexpanded circumference and in a generally opened orientation with respect to each other and with respect to said bendable connecting portions at said expanded circumference; and a plurality of welds join less than all of said adjacent bendable connecting portions of adjacent full circle windings to each other, said welds being present along the length of the endoprosthesis, each of said full circle windings has at least one of said plurality of welds, and the remainder of said adjacent bendable connecting portions are unwelded, and said plurality of welds define a plurality of weld spine patterns which are spaced from one another by ones of said unwelded connecting portions.

2. The endoprosthesis in accordance with claim 1, wherein said weld spine patterns define substantially in-line helical patterns of welds along the endoprosthesis body.

3. The endoprosthesis in accordance with claim 1, wherein said weld spine patterns define two substantially in-line helical patterns of welds along the endoprosthesis body, said helical patterns of welds being longitudinally spaced from each other.

4. The endoprosthesis in accordance with claim 1, wherein said weld spine patterns define three substantially in-line helical patterns of welds along the endoprosthesis body, said helical patterns of welds being longitudinally spaced from each other.

5. The endoprosthesis in accordance with claim 1, wherein said weld spine patterns define a plurality of substantially in-line helical patterns of welds along the endoprosthesis body, said helical patterns of welds being longitudinally spaced from each other.

6. The endoprosthesis in accordance with claim 1, wherein said endoprosthesis body has a length which decreases when the endoprosthesis is expanded from said unexpanded circumference to said expanded circumference.

7. The endoprosthesis in accordance with claim 1, wherein said weld spine patterns define at least one substantially in-line helical pattern of welds following a pitch angle along the endoprosthesis body and defined with respect to the longitudinal axis of the body, and said pitch angle of the in-line helical pattern of welds increases as the endoprosthesis expands from its unexpanded circumference to its expanded circumference.

8. The endoprosthesis in accordance with claim 7, wherein the generally helically wrapped axis of the endoprosthesis body has a helix winding angle defined with respect to the longitudinal axis of the endoprosthesis body, and said helix winding angle increases as said endoprosthesis expands from said unexpanded circumference to said expanded circumference.

9. The endoprosthesis in accordance with claim 1, wherein said repeating pattern of undulations define a generally sinusoidal pattern.

10. The endoprosthesis in accordance with claim 1, wherein said plurality of bendable segments, legs, bendable connecting portions and welds all lie along a single substantially cylindrical plane defined by the endoprosthesis body.

11. The endoprosthesis in accordance with claim 1, wherein said repeating pattern of undulations changes during expansion from said unexpanded circumference to said expanded circumference to define an expanded repeating pattern in which alternating legs of the bendable segments are generally parallel to each other.

12. The endoprosthesis in accordance with claim 1, wherein said welds are fusion welds.

13. The endoprosthesis in accordance with claim 12, wherein the wound strand is tantalum metal, and said fusion welds are formed within a substantially closed atmosphere of inert gas to avoid embrittlement of said fusion weld.

14. The endoprosthesis in accordance with claim 1, wherein the endoprosthesis defines an outwardly facing supporting surface area that comprises between about 12% and about 15% of a cylindrical plane defined by the endoprosthesis, the balance of the cylindrical plane being non-supporting open area.

15. The endoprosthesis in accordance with claim 1, wherein at least one of said weld spine patterns joins all of said adjacent bendable connecting portions by lying along said spine patterns to impart increased hoop strength to said endoprosthesis body while said unwelded connecting portions impart to said endoprosthesis compliance properties to follow contours of vessels within which the endoprosthesis is implanted.

* * * * *